United States Patent [19]
Eross

[11] 3,946,742
[45] Mar. 30, 1976

[54] ENDOTRACHEAL TUBE HOLDER

[76] Inventor: Bela Eross, P.O. Box 397, Bradfordwoods, Pa. 15015

[22] Filed: Oct. 18, 1974

[21] Appl. No.: 515,963

[52] U.S. Cl. ............ 128/351; 128/DIG. 26; 248/75
[51] Int. Cl.² .................. A61M 25/02; A61M 16/00
[58] Field of Search............. 128/208, 351, DIG. 26; 248/75

[56] References Cited
UNITED STATES PATENTS

| | | | |
|---|---|---|---|
| 2,590,006 | 3/1952 | Gordon | 128/DIG. 26 |
| 3,119,587 | 1/1964 | Anderson | 248/75 |
| 3,251,069 | 5/1966 | Clark | 248/75 X |
| 3,312,434 | 4/1967 | Simon | 248/75 X |
| 3,702,612 | 11/1972 | Schlesinger | 128/DIG. 26 X |
| 3,774,616 | 11/1973 | White et al. | 128/DIG. 26 X |

*Primary Examiner*—Channing L. Pace
*Attorney, Agent, or Firm*—Christensen, O'Connor, Garrison & Havelka

[57] ABSTRACT

An endotracheal tube holder includes a support arm mounting a tube retainer, an elongated chin mount that is held by a neck strap against the chin and in turn positions the support arm with the tube holder located between the wearer's teeth. A releasable strap detachably holds the tube in the retainer. A friction pivot connects the base of the arm to the chin mount so as to permit adjustive shifting of the tube retainer transversely across the mouth.

7 Claims, 8 Drawing Figures

U.S. Patent   March 30, 1976   Sheet 1 of 2   3,946,742
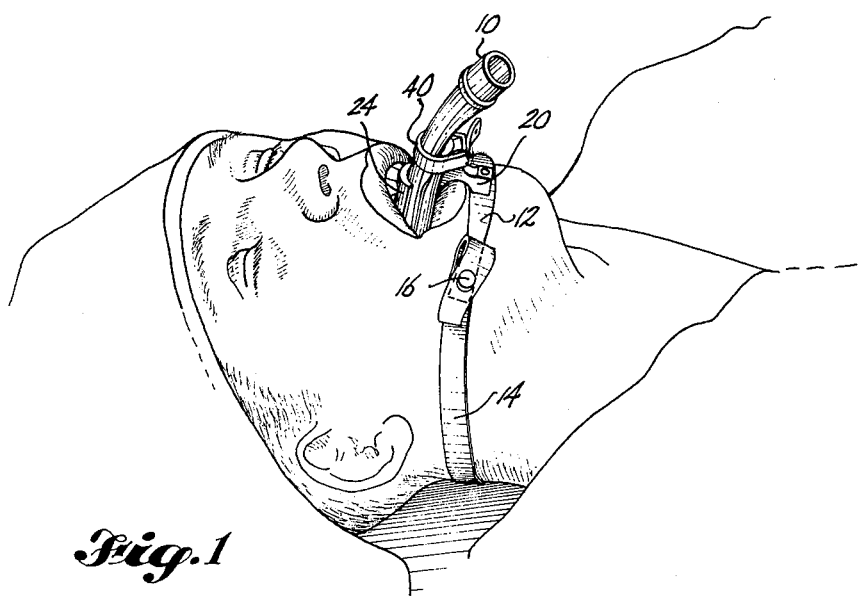
Fig. 1
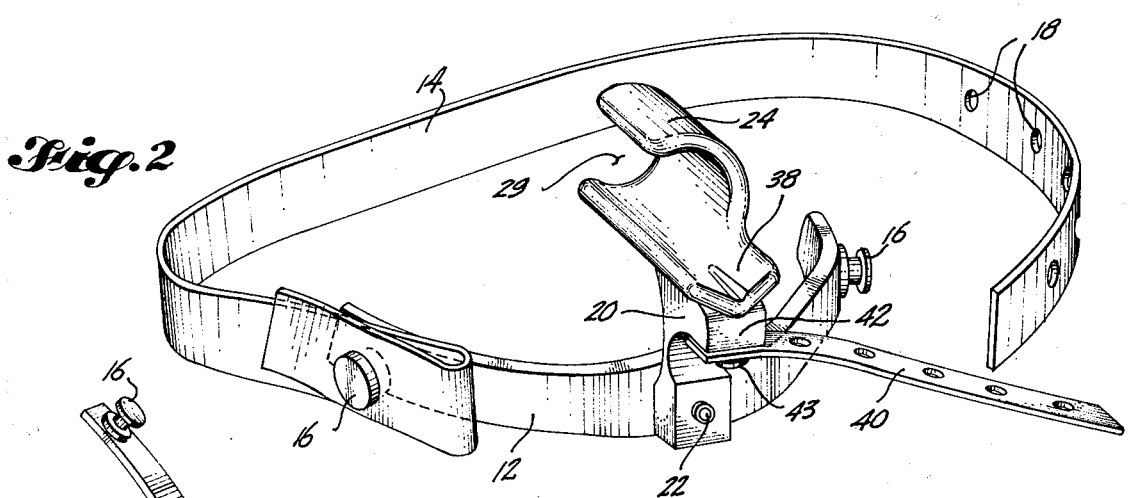
Fig. 2
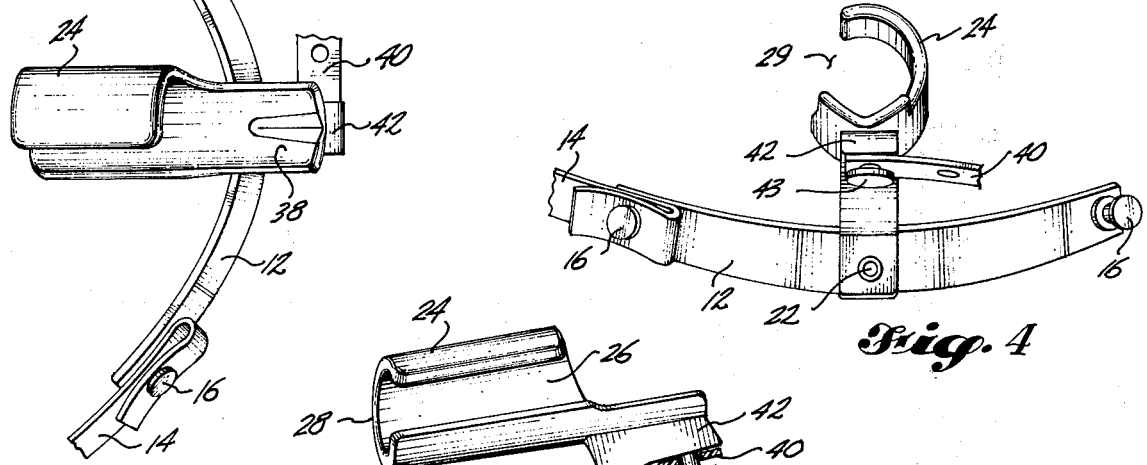
Fig. 3
Fig. 4
Fig. 5

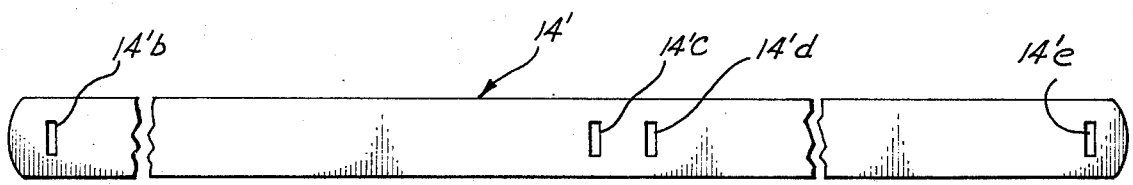
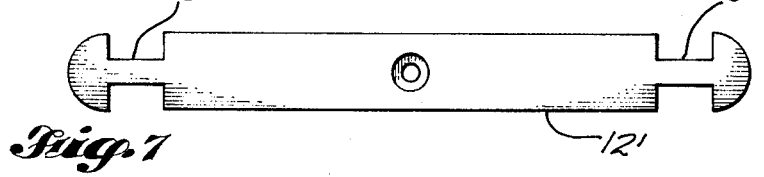
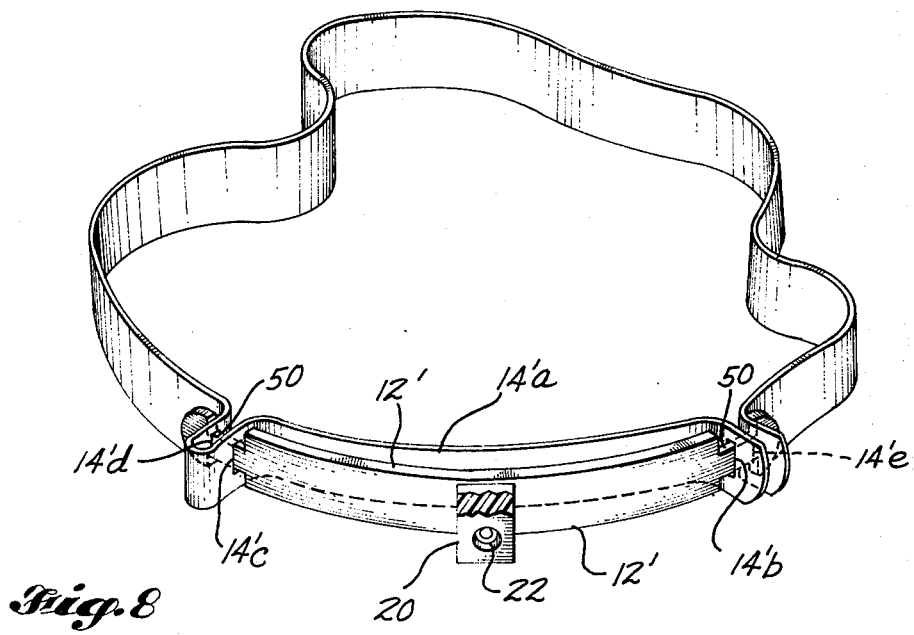

ENDOTRACHEAL TUBE HOLDER

BACKGROUND OF THE INVENTION

This invention relates to medical devices and, more particularly, to an improved holder for endotracheal tubes.

Placement of endotracheal tubes inserted in the patient's trachea typically is maintained by adhesive tape adhered about the tube and over the face and mouth. The tape obstructs access to the mouth and trachea while the tube is in place and makes it difficult to temporarily remove or shift the tube during routine or emergency procedures. Endotracheal tube holders of various types have been devised to overcome the problems encountered with the use of tape. However, prior devices of this type have not been altogether satisfactory because they also substantially or totally obstructed access to the mouth. Examples are illustrated and described in U.S. Pat. Nos. 2,820,457 and 2,693,182 to Phillips. In those cases the tube has to be threaded endwise through a retainer, a procedure that is sometimes awkward and therefore potentially dangerous in an emergency situation. In U.S. Pat. No. 2,908,269 to Cheng there is disclosed a flanged tube holder which has an arcuate slot into and from which a tube may be inserted and withdrawn with the tube holder flange held in position covering the mouth opening. Limited mouth access is provided by a small port through the flange.

It is an object of the present invention, therefore, to overcome these and other disadvantages of such prior art devices by providing an endotracheal tube holder affording substantially improved access to the mouth and trachea, and providing a stable, compact, adaptable supporting assembly for the tube retainer element, quickly and easily secured to the patient regardless of facial characteristics.

Another object is to provide an improved endotracheal tube holder wherein the tube retainer element is adjustively movable in the patient's mouth.

Another object is to devise an endotracheal tube holder that may be installed with the tube already inserted into the patient's mouth, such as in emergency situations, and which permits quickly inserting and removing a tube with the holder in mounted position. It is also important that the tube retainer protect the tube against occlusion between the patient's teeth.

An additional broad object is to provide a versatile, practical, economic and safe endotracheal tube holder applicable to a wide range of medical or surgical conditions and needs.

SUMMARY OF THE INVENTION

In accordance with this invention, the improved oral tube holder comprises a rigid protective tube retainer or bite member supported on an arm connected by a friction pivot to a base or chin mount such that the arm can be swung transversely across the mouth into selected different positions.

The retainer or bite member has a lateral opening through its side and is, preferably, C-shaped in cross-sectional configuration, to permit insertion and removal of a tube transversely of its length. Preferably formed of semi-rigid plastic material, the tube retainer protects the tube against occlusion by being clamped between the patient's teeth.

The slenderness of the support arm and the minimal cross section of the tube retainer minimizes obstruction of the patient's mouth with the holder in place. This allows the physician visual observation and physical access to the oral cavity. The pivotal support for the arm makes it possible to swing the bite member about the mouth with or without the tube in place, so as to further improve accessibility with a tube inserted. In an emergency the endotracheal tube can be inserted first and thereafter the holder can be mounted and the tube secured in the holder without necessity for withdrawing the tube from the trachea or sliding it coaxially through the bite or retainer member. Thus, tubes and holders may be easily installed, removed or interchanged.

These and other objects, advantages, and features of the present invention will become apparent from the detailed description to follow in conjunction with the accompanying drawings.

BRIEF DESCRIPTION OF THE DRAWINGS

FIG. 1 is a perspective view of the tube holder according to the present invention positioned on a patient to hold an endotracheal tube;

FIG. 2 is a perspective view of the tube holder of FIG. 1;

FIG. 3 is a top view of the tube holder of FIG. 1 with strap portions removed; and FIG. 4 is a corresponding front view;

FIG. 5 is a side view, partly in section, of the tube holder of FIG. 1;

FIG. 6 is a face view of an attachment strap of a modified embodiment;

FIG. 7 is a face view of the base member of the modified embodiment; and

FIG. 8 is an assembled view of the modified embodiment with the support arm broken away which carries the tracheal tube holder per se in the modified embodiment.

DETAILED DESCRIPTION OF THE PREFERRED EMBODIMENT

In FIGS. 1–5, wherein like parts bear like reference numerals, there is shown a tube holder suitable for use in maintaining proper placement of an endotracheal tube 10 extending through the mouth between the occlusive portions thereof (i.e. the jaws, teeth, gums, etc.) and into the trachea. As depicted in FIG. 1, the outer end of a tube 10 so positioned by the illustrated tube holder projects upwardly from the mouth of a patient lying face up. It will be apparent that the tube holder of the present invention is suitable for use in other applications in which it is desirable to accurately position and restrain generally similar tubular or elongated medical apparatus insertable into a patient's mouth.

The illustrated tube holder includes a chin mount or base member 12 of elongated generally arcuate form that seats against the chin immediately beneath the lower lip, or if desired, over the upper lip, extending lengthwise in a transverse direction across the face. The ends of the base member 12 are secured to the ends of an adjustable neck strap 14 which holds the chin mount in position by tension in the strap encircling the patient's neck, as depicted in FIG. 1. Button-like fasteners 16 on each end of the base member 12 interconnect the ends of the strap 14 and base member 12. One of the base member fasteners 16 remains connected with one end of the strap by insertion through a hole therein, as shown (FIG. 2). The opposite base member fastener 16 is detachably interengaged with the other end of the strap 14 by entering a selected hole 18 of a series of spaced holes 18 (FIG. 2) formed in that end portion of strap 14. Strap 14 is preferably of elastic material and may have a liner of moisture absorbent material that does contact the wearer's skin, as may the base member 12.

An arm 20 is connected at its lower end by a friction pivot pin 22 to the base member 12 intermediate the ends of the latter (see FIG. 5). The pin 22 is oriented perpendicular to member 12 to permit adjustive swinging of the arm in a plane parallel to the patient's face.

A tracheal tube retainer 24 fixedly mounted on the upper end of the arm 20 projects into the patient's mouth with the arm in its erect position perpendicular to chin mount. The retainer 24 comprises an open sided or C-shaped channel which accommodates a tracheal tube extending through the retainer in a direction parallel to its axis.

The lateral or side opening 29 in tube retainer 24 (see FIG. 4) extends it full length and thereby permits direct transverse insertion and removal of tracheal tubes in the retainer. It is desirable that its lateral opening 29 have a width smaller than the diameter of the elastic tracheal tube 10 so that once forced through the opening, the tube 10 tends to remain in the retainer channel. However, for more secure retention, an elastic tube retaining strap 40 is used to hold the tube 10 in place positively. Strap 40 is secured by one end to the underside of a shoulder 42 projecting transversely from the supporting arm 20 oppositely to the holder but in alignment with its bottom wall. Shoulder 42 underlies a tube retainer segmental forward extension in the form of a troughed clamping surface 38 over which a tracheal tube extends in passing through the retainer proper. Strap 40 stretched around the tube and shoulder is made fast by its opposite end on a button 43 projecting downwardly from the arm shoulder 42.

The base member 12, arm 20 and bite member 24 typically are formed of a plastic material suitable for sterilization by heat treatment, chemicals, etc.

The base member 12 preferably comprises a thin, stiff, plastic strip sufficiently flexible that when under tension drawn by the nect strap it will lie flat against and conform to the face adjacent the mouth and stably hold the arm 20 and the tube retainer 24 in position during use. If desired, the neck strap 14 may be replaced by equivalent securement means such as by taping it to the face; hence in an emergency such as if the strap 14 is lost or broken the tube retainer carried by arm 20 on base member 12 is fully usable.

Preferably the retainer member 24 is formed of plastic material having sufficient stiffness to resist deformation and collapse when clamped between the patient's teeth. Because it will often be bitten it should be stiff enough to avoid injury to the teeth or gums and for that purpose also may be covered with a softer protective layer (not shown) such as a soft rubber-like material.

As best shown in FIG. 1, the retainer or bite member 24 in use is normally positioned by the base member 12 and arm 20 so that it projects rearwardly generally centrally into the oral cavity. In this operative position, its rear and forward ends 28 and 26 (see FIG. 5) are located respectively inside and outside the teeth thus forming a shield for the tube 10 which it holds. The tube 10 may be interengaged with and disengaged from the bite member 24 through the lateral opening 29 with the tube already inserted and with the tube holder in this position or in process of being placed there or of being itself removed. Thus other tubes and other elements or articles may be substituted for the illustrated tube 10 without disturbing placement of the bite member. These may differ in size and form cross-sectionally because the open-sided or longitudinally slotted form of the retainer as a holder channel and the use of securement strip 40 lends added versatility to the holder. The bite member or retainer 24 supported on the upper end of the arm 20 is long enough that a portion of it will remain between the patient's teeth to protectively shield the tube 10 from occlusion even with the retainer swung fully to the side of the mouth. It also will be apparent that the minimal exterior cross section and compactness of the bite member 24 and the arm 20 minimize obstruction of the oral cavity and oral orifice.

With reference to the modified embodiment shown in FIGS. 6, 7 and 8, the curved base member 12' which fits against the patient's face has rounded ends and is necked down in width to form notches 50 in both edges adjacent the ends. The flexible neck strap 14' is devised in this case for simplicity of manufacture and for use as a cushioning element. For this latter purpose a length portion 14'a underlies the base member between the opposite end notches 50 and is held in this position by elastic retention of the notched parts of the base member in apertures in the strap. Thus a slot 14'b in one end of the strap is slipped over one headed end of the base member as depicted at the right in FIG. 8. From this securement the strap extends along the back side of the base member to double slots 14'c and 14'd, where the strap is folded between slots to slip the latter over the headed opposite end of the base member with the fold projecting outward. The strap extends from there around the head of the patient, and its opposite end, provided with a slit 14'e (or a series of successively spaced slits for adjustable tensioning of the strap) secures to the notched first end of the base member. An inexpensive plain rubber strap without separate fasteners or snaps, therefor, performs the securement function and provides a safe, compatible and convenient means of attachment. The tracheal tube holder and support parts not shown in FIG. 8 may be similar to those shown in the preceding figures.

it will be appreciated that various other modifications and/or changes can be made in the endotracheal tube holder, that the foregoing description and drawings are illustrative and not limiting, and that the spirit and scope of the present invention is to be determined by reference to the appended claims.

What is claimed is:

1. An endotracheal tube holder comprising an endotracheal tube retainer member of elongated form adapted for operative positioning in a patient's mouth extending outwardly therefrom between the patient's teeth to serve as a bite protecting a tube retained therein against being clamped shut between the teeth, said retainer member being adapted to be shifted transversely of its length from side to side in the patient's mouth, and mounting means for the retainer member including base means formed to be seated against the patient's face adjacent to and extending along one lip, securing means engageable with the patient's head for holding the base means securely thus seated, and a support arm rigidly connected to the retainer member in mutually transverse relationship and movably connected to the base means to be supported thereby while permitting transverse movement of the arm to effect the aforesaid shifting of the operatively positioned retainer member.

2. The holder according to claim 1 wherein the base means comprises an elongated seating member that flexes into substantial conformity with the patient's facial contour, the arm being pivotally connected to such seating member intermediate the ends of the latter.

3. The holder according to claim 2 wherein the securing means comprises a neck-encircling strap engaging opposite ends of said elongated seating member and adapted to extend around the patient's neck to hold said seating member under tension seated against the patient's face.

4. The holder according to claim 3, wherein the elongated retainer member is of semi-tubular form with a side opening extending from end to end thereof to permit insertion and removal of an endotracheal tube through said opening by moving the tube in a relatively transverse direction.

5. The holder according to claim 1, wherein the elongated retainer member is of semi-tubular form with a side opening extending from end to end thereof to permit insertion and removal of an endotracheal tube through said opening by moving the tube in a relatively transverse direction.

6. The holder defined in claim 5 wherein the retainer member includes a longitudinal extension adapted to project outwardly in relation to the patient's mouth and of open trough-like form for seating of an endotracheal tube therein which extends through the retainer member, and attachment means on said retainer member adapted for releasibly securing the endotracheal tube seated in said trough-like extension.

7. The holder defined in claim 4 wherein the retainer member includes a longitudinal extension adapted to project outwardly in relation to the patient's mouth and of open trough-like form for seating of an endotracheal tube therein which extends through the retainer member, and attachment means on said retainer member adapted for releasibly securing the endotracheal tube seated in said trough-like extension.

* * * * *